(12) United States Patent
Kawabata et al.

US006299911B1

(10) Patent No.: US 6,299,911 B1
(45) Date of Patent: Oct. 9, 2001

(54) EXTRACT OF TOUCHI CONTAINING AN α-GLUCOSIDASE INHIBITOR

(75) Inventors: Jun Kawabata; Takanori Kasai, both of Sapporo; Hiroyuki Fujita; Nobuhiro Fukushima, both of Ibaraki, all of (JP)

(73) Assignee: The Nippon Synthetic Chemical Industry Co., Ltd., Osaka (JP)

( * ) Notice: Subject to any disclaimer, the term of this patent is extended or adjusted under 35 U.S.C. 154(b) by 0 days.

(21) Appl. No.: 09/530,063

(22) PCT Filed: Aug. 20, 1999

(86) PCT No.: PCT/JP99/04466

§ 371 Date: Apr. 24, 2000

§ 102(e) Date: Apr. 24, 2000

(87) PCT Pub. No.: WO00/12109

PCT Pub. Date: Mar. 9, 2000

(30) Foreign Application Priority Data

Aug. 26, 1998 (JP) .................................................. 10-239326
Jul. 1, 1999 (JP) .................................................. 11-187634

(51) Int. Cl.[7] ............................. A61K 35/78; C12N 9/00; C12N 9/24
(52) U.S. Cl. ........................... 424/757; 435/183; 435/200
(58) Field of Search ................................ 424/195.1, 757; 435/183, 200

(56) References Cited

U.S. PATENT DOCUMENTS 6,045,819 * 4/2000 Takebe ................................. 424/442

FOREIGN PATENT DOCUMENTS 682 877 A1    11/1995  (EP) .
9065836        3/1997  (JP) .
WO 97/37549 * 10/1997  (JP) .

OTHER PUBLICATIONS

Kiuchi et al., J. Agric. Food Chem., vol. 24, No. 2, pp. 404–407, 1976.*

* cited by examiner

Primary Examiner—David M. Naff
Assistant Examiner—Mike Meller
(74) Attorney, Agent, or Firm—Armstrong, Westerman, Hattori, McLeland & Naughton, LLP

(57) ABSTRACT

An α-glucosidase inhibitor is described. It is comprised of an extract of Touchi selected from the group consisting of an extract of Touchi extracted with alcohol, an extract of Touchi extracted with a mixture of water and alcohol in a water to alcohol ratio of 1:5 to 5:1, and an extract of Touchi extracted with water at 100° C. to 140° C. The components in the extract which have a molecular weight of at least 3000 as determined by means of gel filtration or membrane filtration are at most 20% by weight and wherein the extract inhibits α-glucosidase at least 90.4%.

1 Claim, No Drawings

EXTRACT OF TOUCHI CONTAINING AN α-GLUCOSIDASE INHIBITOR

TECHNICAL FIELD

The present invention relates to an α-glucosidase inhibitor containing Touchi as an active ingredient, which can be used in pharmaceuticals, food products, health foods, particular health care foods and the like.

BACKGROUND OF THE INVENTION

It is described that an α-glucosidase inhibitor inhibits an α-glucosidase which is localized at a fine villus in a small intestine, and controls a rapid increase in blood sugar after meal and next increase in insulin level (Diabate Medicine, 10, 688 (1993)). Since it suppresses metabolism of a carbohydrate (especially oligosaccharide derived from starch, sucrose and the like) also in human and the other animals, and exhibits an inhibitory effect of blood sugar increase, it is effective in improving a hyperglycemic condition as well as various diseases induced by a hyperglycemia such as obesity and diabetes. And a food product obtained by adding α-glucosidase thereto is a suitable meal for a patient having a symptom and also for a healthy human on the purpose of prophylaxis against such symptom.

As an α-glucosidase inhibitor derived from a food, for example, a enzymatic hydrolysate of an animal protein or a vegetable protein were disclosed in Japanese Unexamined Patent Publication No. 9-65836(1997) and tea polyphenol was disclosed in Japanese Unexamined Patent Publication No. 5-17364(1993).

However, the α-glucosidase inhibitor disclosed in Japanese Unexamined Patent Publication No. 9-65836(1997) had a problem that it should be taken in a large amount as a food for exerting its activity. And the α-glucosidase inhibitor disclosed in Japanese Unexamined Patent Publication No. 5-17364(1993) had problems that it was complicated to purify polyphenol and it was necessary to take a large amount in case of routinely consumed tea. An object of the present invention is to provide an excellent α-glucosidase inhibitor, which has a high activity and can readily be ingested.

DISCLOSURE OF THE INVENTION

We made an effort to solve the problems described above and finally discovered that Touchi, which is used as an ingredient of Chinese food, had an excellent α-glucosidase inhibitory activity to complete the present invention.

Namely, the present invention relates to an α-glucosidase inhibitor comprising Touchi as an active ingredient (Claim 1);

the α-glucosidase inhibitor of Claim 1, characterized in an extract obtained by extraction of Touchi with water and/or alcohol is used as Touchi (Claim 2), and the α-glucosidase inhibitor of Claim 2, wherein an amount of a component having a molecular weight of at least 3000 in said extract obtained by extraction with water and/or alcohol is at most 20% by weight (Claim 3).

BEST MODE FOR CARRYING OUT THE INVENTION

Touchi employed in the present invention is usually one obtained by steaming a soybean and fermenting it with koji (Aspergillus). And Touchi includes Daitokuji natto, Hama natto, Tera natto, Shiokara natto, Ikkyuji natto that are fermented soybeans and the like in Japan.

While an ordinary fermentation is performed by preserving in salt, a product similarly produced without salt or a product desalted at completion of the fermentation may also be employed in the present invention.

Touchi is used in an ordinary form, and powder obtained by pulverizing after drying and slurry obtained by pulverizing in water also exhibit a glucosidase inhibitory effect. But extracts obtained by extraction of Touchi with water and/or alcohol are preferable from the viewpoint of exhibiting a potent α-glucosidase inhibitory activity.

Examples of the alcohol employed for extraction are methanol, ethanol, propanol, butanol and the like. Methanol and ethanol are preferable. Examples of the extraction method are stirring extraction, preserving extraction, supercritical extraction and the like. Usually stirring extraction or immersing extraction is employed. When water and alcohol are employed in a combination use, a ratio (weight) of water to alcohol is preferably 1/10 to 10/1, more preferably 1/5 to 5/1.

When the extraction is conducted with water, to Touchi as it is or Touchi obtained by pulverizing is added water in an amount of 1 to 20 times, and Touchi is extracted by stirring extraction at 40 to 60° C. for 12 to 20 hours, or at 100 to 140° C. for 1 to 3 hours.

When the extraction is conducted with alcohol or a combination of water and alcohol, to Touchi as it is or Touchi obtained by pulverizing is added alcohol or a mixture of water and alcohol in an amount of 1 to 15 times, and Touchi is extracted by immersing extraction at 40 to 60° C. for 3 to 10 hours, or at a room temperature for 10 hours to 7 days. If necessary, water and alcohol can be distilled off to adjust a concentration thereof.

An extract obtained after the above extraction step can be used as it is. Alternatively, it may be used in the form of powder after distilling water and alcohol.

The extract usually contains 30 to 90% by weight of the components having a molecular weight of at least 3000, as discussed later.

In order to obtain an effect by ingestion in a small amount, an extract may be subjected to a solvent fractionation using a polar organic solvent such as methanol, ethanol, propanol, butanol, chloroform, ethyl acetate, toluene, hexane or benzene to concentrate an active component, or may be purified by at least one suitable purification method selected from the group consisting of alumina column chromatography, silica gel column chromatography, ion exchange chromatography, hydrophobic chromatography, and high performance liquid chromatography.

In the invention, it is preferable that an amount of the components having a molecular weight of at least 3000 is at most 20% by weight in the extract obtained by water and/or alcohol extraction of Touchi described above from the viewpoint of exhibiting an excellent glucosidase inhibitory activity. Concretely, it is preferable to use a product obtained by removing any components having a molecular weight of at least 3000 from the above extract to be in an amount of at most 20% by weight thereof (hereinafter referred to as "purified product"), more preferably 0.1 to 15% by weight.

The above-mentioned molecular weight of the sample is measured by a gel filtration chromatography. Concretely, using an amino acid, a peptide and a protein [Ala (molecular weight 89), Ile-Tyr (molecular weight 330), Asp-Gly-Leu-Tyr-Pro (molecular weight 563), neurotensin (molecular weight 1637), and ribonuclease (molecular weight 13700) as s standard reference, which have the known molecular weights, an extract is eluted in the following conditions to determine a retention time, and a molecular weight is determined by using a calibration curve obtained by plotting the molecular weights on the ordinate and the retention times on the abscissa logarithmically.

In the invention, an amount "% by weight" of the components having a molecular weight of at least 3000 is represented as "% area" of the peaks corresponding to components having a molecular weight of at least 3000 after dividing the peaks at the position of the molecular weight 3000 on an elution chromatogram.

(Fraction Conditions)
Column: Protein Pak60 (made by Waters) 5×250 mm
Mobile phase: 50% by volume acetonitrile aqueous solution containing
   0.1% by volume TFA (trifluoroacetic acid)
Flow rate: 1 mL/min
Detection: RI
Sample amount: 1 mg

TABLE 1

Relationship between molecular weight and elution time

| Standard substance | Molecular weight | Elution time (minutes) |
|---|---|---|
| Ala | 89 | 37 |
| Ile—Tyr | 330 | 33 |
| Asp—Gly—Leu—Tyr—Pro | 563 | 31 |
| Neurotensin | 1637 | 26 |
| Ribonuclease | 13700 | 19 |

In the above-mentioned conditions, since a substance having a molecular weight of 3000 is eluted at 25 minutes, any substance eluted at not more than 25 minutes is regarded as components having a molecular weight of at least 3000.

The followings are examples of a method for removing a component having a molecular weight of at least 3000.

[1] a method for removing fractions having a molecular weight of at least 3000 by means of a gel filtration chromatography

[2] a method for removing fractions having a molecular weight of at least 3000 by means of a membrane treatment

[3] a method for removing fractions having a high molecular weight by a solvent extraction using a polar organic solvent such as methanol, ethanol, propanol, butanol, chloroform, ethyl acetate, toluene, hexane or benzene.

These methods can be used solely or in a combination use of two or more thereof.

The methods [1] to [3] are explained briefly.

In the method [1, the procedure described above as a molecular weight analysis is performed in an industrial scale.

In the method [2], an extract is filtered through a membrane having a fractionation molecular weight of about 3000 (UF membrane), such as UF membrane "PLBC (fractionation molecular weight 3000)" available from Millipore, and UF membrane "SEP1013 (fractionation molecular weight 3000)" available from Asahikasei.

In the method [3], an extract obtained by extraction with water and/or alcohol is concentrated to such an extent that no precipitation appears, 5 to 10 volumes of alcohol is added thereto to precipitate any substance having a high molecular weight.

The obtained α-glucosidase inhibitor of the present invention has an inhibitory effect on a blood sugar increase. Therefore, it can be used as a pharmaceutical formulation such as ampule, granule, pill, capsule or syrup ; a health food such as a meal for a patient having a symptom as well as a prophylactic agent therefor, a diabetes preventing agent, an anti-obesity agent, a diet food and the like, which are obtained by diluting with a carrier having no toxicity such as; a liquid carrier such as water, ethanol, ethylene glycol or poly(ethylene glycol), and a solid carrier such as starch, cellulose or polyamide powder. In addition, an increase in the blood sugar level caused by taking meals can be inhibited by taking the above formulation containing an α-glucosidase inhibitor of the present invention before, during, after and between meals.

An amount of Touchi taken in by a human is preferably 1 to 50 g per day, more preferably 5 to 10 g per day. In case of the extract obtained by extraction with alcohol, the amount may be 1/10 of that of Touchi as it is.

A purified product is preferably taken in an amount of 0.00001 to 5 g per day, especially 0.005 to 0.5 g per day converted to the dried product basis, since it has an inhibitory activity 2 to 1000 times more than that of the extract obtained by extraction with water and/or alcohol.

An α-glucosidase inhibitor of the present invention can also be added to a food product as the following.

(1) Processed Agricultural and Marine Products gelatin noodle, pureed sweet re-bean jam, a gelatinous food made from devil's-tongue starch, bread, noodles (instant noodle, pasta, raw noodle, dried noodle), rice cake, cereals, processed soybean products (tofu, soybean milk, natto, dried bean curd), processed marine products [boiled fish paste, (crab-flavored) fish string sausages, (fish) ham, (fish) sausage, (fish) wieners, rice topping, layer flakes for rice with tea], foods containing egg (soup, rice bowl and the like), canned foods (canned tuna, oil-preserved sardines, yakitori skewers), retort-packed foods (curry, stew, spaghetti sause)

(2) Dairy Products milk, processed milk, lactic fermented beverage, butter, cheese, condensed milk, powdered milk (3) Seasoning miso(fermented soybean paste), soy sauce, flavoring and seasoning, (powdered) natural seasoning, sauce, dressing, barbecue sauce, sweet sake seasoning, curry, stew, hot and mild spice, yogurts (4) Health Foods (nutrition supplement)

1] food containing Saponin (food containing Panax ginseng root, food containing Acanthopanax Senticosus Harms)

2] food containing saccharide [oligosaccharide (food containing fluctooligosaccharide, food containing isomaltooligosaccharide, food containing galactooligosaccharide), polysaccharide (food containing Cortinellus shiitake, muco saccharide, food containing protein, food containing chondroitin sulfate, food containing Ganoderma lucidium (Reishi), food containing chitin/chitosan)

3] food containing mineral (food containing calcium, food containing alfalfa, food containing prune extract, food containing β-carotene)

4] food containing fat (fat containing vitamin E [wheat and tear grass germ oil, soybean germ oil, rice germ oil], food containing eicosapentaenoic acid, food containing soybean lecithin, food containing γ-linolenic acid (evening primrose oil, borage oil), food containing docosahexaenoic acid)

5] food containing protein (food containing soybean protein, casein, whey protein, processed carp)

6] food containing taurine oyster, processed corbicula, processed green sea mussel (5) Others Processed soft-shelled turtle, amino acid dysbolism-oriented food, liquid food (patient's meal)

It is possible to add it to a food containing a large amount of the following saccharides, but there is a case that the inventive effect is not expressed clearly. It is preferable to reduce a saccharide content of an intended food to a level as low as possible in case of adding the following foods.

(6) Confectionery

Cake, mousse, (powdered) dessert, ice cream, candy, chocolate, gumdrop, cookie, wafer, jelly.

(7) Beverage

Refreshing beverage (carbonated beverage, fruit juice, sport supplement beverage, health drink), luxury beverage (coffee, cocoa drink, barley beverage), miso soup, clear soup In the above-mentioned (1) to (7) an amount of Touchi is preferably 1 to 85% by weight, more preferably 10 to 60% by weight in the above-mentioned food. When an extract with water and/or alcohol is used, the amount may be 1/10 (by weight) of that of Touchi itself. Especially when purified Touchi is employed, the amount is preferably 0.00001 to 20% by weight, more preferably 0.001 to 10% by weight.

In addition, additives such as sweetener, preservative, dispersant, colorant and antioxidant may also be added as long as they do not affect the inventive effect adversely. Furthermore, another known α-glucosidase inhibitors such as Varienamine and Aminocyclitol may also be incorporated.

The present invention is further explained below. In the following description, "%" means "% by weight", unless otherwise indicated.

EXAMPLE 1

One kg of dried Touchi was immersed in 10 L of a 50% methanol aqueous solution for one day. The obtained exudate was concentrated by using a rotary evaporator, and dissolved in water and filtered. The obtained filtrate was concentrated under a reduced pressure to obtain an extract (E-1).

The extract was evaporated into dryness using a rotary evaporator to obtain 19.3 g of a solid. The solid was placed in a separation funnel and combined with a mixture of ethyl acetate and water (volume ratio ½) in an amount of 5 times larger than that of the solid. And it was partitioned between an aqueous layer (E-2) and an ethyl acetate layer (E-3) to examine an α-glucosidase inhibitory activity.

The α-glucosidase inhibitory activity in each fraction (E-1, E-2 and E-3) was determined as described below.

(1) Preparation of di- (tri-)saccharide Hydrolase (α-glucosidase) from Rat Small Intestine A rat small intestine (jejunum) which had been stored frozen was thawed and mucosa was collected by pushing it out using tweezers. To the mucosa was added a 0.1 M potassium phosphate buffer (pH7.0) containing 5 mM ethylenediamine tetraacetic acid in an amount of 5 times larger than that of the mucosa and the mixture was homogenized with cooling. Subsequently, the mixture was centrifuged (4° C., 21000×g, 60 minutes), to the obtained precipitate was added 0.1 M potassium phosphate buffer (pH7.0) containing 1% Triton X-100 in an amount that the total amount of mixture becomes five times larger than the precipitate to carry out solubilization (4° C., 60 minutes). The mixture was ultracentrifuged (4° C., 110000 ×g, 90 minutes) and the supernatant was dialyzed (4° C., 24 hours) with 0.01 M potassium phosphate buffer solution (pH7.0) to obtain an enzyme solution.

(2) Enzyme (α-glucosidase) activity assay

The enzyme activity was determined by using a commercial kit together with sucrose as a substrate.

A standard reaction mixture (1.0 ml in total) contained 0.7 ml of 60 mM substrate solution (sucrose dissolved in a 0.1 M potassium phosphate buffer solution, pH6.3), 0.2 ml of a tested substance solution (after removing water and the organic solvent completely, followed by dissolving in 50% dimethyl sulfoxide aqueous solution) and 0.1 ml of the above enzyme solution. This was allowed to react at 37° C. for 15 minutes, and then quenched with 1.5 ml of 2M Tris-hydrochloride buffer solution (pH7.0) to obtain a test solution.

Subsequently, to each well of a microplate with 96 wells was added 200μl of a color development reagent [Glucose B Test Wako (available from Wako Pure Chemical)] and 50 μl of the test solution (after distilling a solvent such as ethyl acetate), and the mixture was incubated at 37° C. for 30 minutes. And then an absorbance at 490 nm was measured by using a microplate reader (MODEL 550 made by BIO RAD). An absorbance of a sample containing the 0.1 M potassium phosphate buffer (pH6.3) instead of the substrate solution was used as a blank value, a difference between these two values was indicated as $A_{490S}$. An absorbance of a sample containing 50% by weight of dimethylsulfoxide aqueous solution instead of the test solution was used as a control value ($A_{490C}$), and the α-glucosidase inhibitory activity was calculated according to the following equation. The determination was performed in duplicate, and the mean value was used as the measured value.

α-Glucosidase inhibitory activity (%)={($A_{490C}$−$A_{490S}$)/$A_{490C}$}× 100

The α-glucosidase inhibitory activity of each fraction (E-1, E-2, E-3) is indicated in Table 2.

Yields shown in the table are relative values of each fraction based on the weight of the starting material, which is obtained by concentration into dryness.

TABLE 2

| Fraction | Yield (%) | Concentration of test (mg/ml) | α-glucosidase inhibitory activity (%) |
| --- | --- | --- | --- |
| E-1 | 19.3 | 20 | 92.2 |
| E-2 | 16.5 | 20 | 91.4 |
| E-3 | 2.8 | 20 | 10.8 |

EXAMPLE 2

Thirty gram of aliquot in 193 g of the dried concentrate of Fraction (E-1) obtained in Example 1 was treated with a membrane in the following conditions and a membrane-concentrated fraction (E-5) was removed to obtain a membrane-penetrating fraction (E-4), which was concentrated into dryness to obtain 5.8 g of a dried solid. A molecular weight of the membrane-penetrating fraction (E-4) was measured to find that an amount of the components having a molecular weight of at least 3000 was 15%.

Similarly as in Example 1, the α-glucosidase inhibitory activity was measured and is indicated in Table 3.

Yields shown in the table is a relative value of each fraction based on the weight of the starting material, which are obtained by concentration into dryness.

(Membrane treatment conditions)
Instrument: REMOLINO (made by Millipore)
Membrane: PLBC (fractional molecular weight 3000, made by Millipore)
Pressurizing condition: Under 5 kg with nitrogen gas

TABLE 3

| Fraction | Yield (%) | Concentration of test (mg/ml) | α-glucosidase inhibitory activity (%) |
|---|---|---|---|
| E-1 | 19.3 | 20 | 92.2 |
| E-4 | 3.7 | 0.2 | 90.4 |
| E-5 | 15.6 | 20 | 12.7 |

An amount of the components having a molecular weight of at least 3000 in E-1 was 80%.

EXAMPLE 3

Thirty gram of aliquot in 193 g of the dried concentrate of fraction (E-1) obtained in Example 1 was dissolved in 100 mL of water and ethanol was added at 95% by volume. The mixture was allowed to stand at a room temperature overnight, and a formed precipitate was removed as fraction (E-6) by filtration and ethanol in the filtrate was distilled off under reduced pressure to obtain 4.2 g of fraction (E-7). A molecular weight of fraction (E-7) was measured to find that the components having a molecular weight of at least 3000 was 5%.

Similarly as in Example 1, the α-glucosidase inhibitory activity was determined and is indicated in Table 4.

TABLE 4

| Fraction | Yield (%) | Concentration of test (mg/ml) | α-glucosidase inhibitory activity (%) |
|---|---|---|---|
| E-1 | 19.3 | 20 | 92.2 |
| E-6 | 16.6 | 20 | 9.4 |
| E-7 | 2.7 | 0.1 | 90.8 |

Yields shown in the table are relative values of each fraction based on the weight of the starting material, which is concentrated into dryness.

EXAMPLE 4

One kg of dried Touchi was immersed in 10 L of water and then heated at 130° C. for 1 hour for sterilization. The obtained exudate was filtered and the filtrate (E-8) was concentrated into dryness by using a rotary evaporator to obtain 215 g of a solid.

Thirty gram of aliquot in 215 g of the dried concentrate of fraction (E-8) was treated with membrane in the same manner as in Example 2 to obtain 5.5 g of a membrane-penetrating fraction (E-9) and a membrane-concentrated fraction (E-10). A molecular weight of the membrane-penetrating fraction (E-9) was measured to find that an amount of the components having a molecular weight of at least 3000 was 9.7%. Similarly as in Example 1, the α-glucosidase inhibitory activity was determined and is indicated in Table 5.

Yields shown in the table are relative values of each fraction based on the weight of the starting material, which is concentrated into dryness.

TABLE 5

| Fraction | Yield (%) | Concentration of test (mg/ml) | α-glucosidase inhibitory activity (%) |
|---|---|---|---|
| E-8 | 21.5 | 20 | 91.8 |
| E-9 | 3.9 | 0.2 | 90.8 |
| E-10 | 17.6 | 20 | 13.3 |

Since the α-glucosidase inhibitor of the present invention contains Touchi as an active ingredient, it can readily be ingested and exhibits a potent inhibitory activity.

INDUSTRIAL APPLICABILITY

There is provided an α-glucosidase inhibitor which can readily be ingested and exhibits a potent inhibitory activity. Since an α-glucosidase inhibitor of the present invention contains Touchi as an active ingredient, it can readily be ingested and exhibits a potent inhibitory activity. Because of containing Touchi (Chinese fermented soybean) as the active ingredient, this α-glucosidase inhibitor can be easily taken and shows a potent inhibitory activity.

What is claimed is:

1. An α-glucosidase inhibitor comprising an extract of Touchi selected from the group consisting of an extract of Touchi extracted with alcohol, an extract of Touchi extracted with a mixture of water and alcohol in a water to alcohol ratio of 1:5 to 5:1, and an extract of Touchi extracted with water at 100° C. to 140° C., wherein components having a molecular weight of at least 3000 as determined by means of gel filtration or membrane filtration in said extract are at most 20% by weight and wherein said extract inhibits α-glucosidase at least 90.4%.

* * * * *